United States Patent
Hopf et al.

(10) Patent No.: US 8,695,624 B2
(45) Date of Patent: Apr. 15, 2014

(54) MULTI-WAY VALVE AND METHOD OF PRODUCING SAME

(75) Inventors: Hans Juergen Hopf, Zirndorf (DE); Norbert Kassai, Oberasbach (DE); Alexander Hopf, Nuernberg (DE); Michael Hopf, Zirndorf (DE)

(73) Assignee: Hans Jürgen Hopf Besitzgesell-Schaft, Zirndorf (DE)

( * ) Notice: Subject to any disclaimer, the term of this patent is extended or adjusted under 35 U.S.C. 154(b) by 106 days.

(21) Appl. No.: 13/383,754

(22) PCT Filed: Jul. 14, 2010

(86) PCT No.: PCT/EP2010/060150
§ 371 (c)(1),
(2), (4) Date: Jan. 12, 2012

(87) PCT Pub. No.: WO2011/006934
PCT Pub. Date: Jan. 20, 2011

(65) Prior Publication Data
US 2012/0103448 A1    May 3, 2012

(30) Foreign Application Priority Data
Jul. 14, 2009 (DE) .................. 10 2009 026 172

(51) Int. Cl.
*A61M 39/22* (2006.01)

(52) U.S. Cl.
USPC ................. 137/315.09; 137/625.47; 251/297; 604/32; 604/236; 604/248

(58) Field of Classification Search
USPC ........... 137/315.09, 625.47; 251/297; 604/32, 604/236, 248
See application file for complete search history.

(56) References Cited

U.S. PATENT DOCUMENTS 3,481,367 A  12/1969  Deuschle
5,207,641 A   5/1993  Allton
(Continued)

FOREIGN PATENT DOCUMENTS

CN    2289101 Y    8/1998
(Continued)

OTHER PUBLICATIONS

English Translation of International Preliminary REport of Patentability for PCT/EP2010/060150, Jul. 14, 2010.
(Continued)

*Primary Examiner* — John K Fristoe, Jr.
*Assistant Examiner* — Kevin Barss
(74) *Attorney, Agent, or Firm* — Factor Intellectual Property Law Group, Ltd.

(57) ABSTRACT

The present invention relates to a multi-way valve for use in medicine or medical technology, having at least one basic housing through which a medium can flow in sections, and having an actuator which is held in said basic housing so as to be rotatable about a central axis, wherein the basic housing has at least two connection points for the inflow and outflow of the medium and forms an actuator receptacle which has a peg arranged concentrically with respect to the central axis and which has, on the inner side of the basic housing, a radially encircling cutout, and wherein the actuator has a control element, a substantially hollow cylindrical section which receives the peg of the actuator receptacle at least in sections, at least one throughflow opening for the fluidic connection between two connection points, and at least one radially encircling molding on the outer side of the cylindrical section, and wherein the peg of the actuator receptacle has at least one counterbearing for the actuator to form a sealing surface in the region of at least one connection point. The invention is characterized in that the peg has at least one flattened portion on the circumference relative to the central axis, and the molding of the actuator engages into the cutout of the actuator receptacle in order to fix the actuator in the actuator receptacle in a positively locking and fluid-tight manner.

17 Claims, 5 Drawing Sheets

(56) References Cited

U.S. PATENT DOCUMENTS

| | | | |
|---|---|---|---|
| 7,152,845 B2 * | 12/2006 | Carrez et al. | 251/297 |
| 2001/0025942 A1 | 10/2001 | Lotz | |
| 2006/0033066 A1 | 2/2006 | Carrez | |
| 2007/0191760 A1 * | 8/2007 | Iguchi et al. | 604/32 |

FOREIGN PATENT DOCUMENTS

| | | |
|---|---|---|
| CN | 2666473 Y | 12/2004 |
| CN | 2928125 Y | 8/2007 |
| DE | 17 50 867 A | 5/1971 |
| DE | 35 03 044 A1 | 7/1986 |
| DE | 20005691 U1 | 6/2000 |
| DE | 200 05 691 U1 | 8/2000 |
| DE | 20 2007 014342 U1 | 1/2009 |
| GB | 1 344 166 | 1/1974 |
| GB | 1 344 166 A | 1/1974 |
| GB | 1 357 424 | 6/1974 |
| TW | 486553 B | 5/2002 |
| WO | 03/093704 A1 | 11/2003 |
| WO | 2004/031635 A1 | 4/2004 |
| WO | WO 2004031635 A1 | 4/2004 |

OTHER PUBLICATIONS

German Search Report issued for DE 10 2009 026 172.9 (priority claimed in the present application) on Feb. 12, 2012.
Patent Office of the Peoples Republic of China, Office Action for Application No. 201080031955.3, dated Mar. 27, 2013.

* cited by examiner

MULTI-WAY VALVE AND METHOD OF PRODUCING SAME

RELATED APPLICATIONS

This application claims the filing benefit of International Patent Application No. PCT/EP2010/060150, filed Jul. 14, 2010, which claims the filing benefit of German Patent Application No. 10 2009 026 172.9 filed Jul. 14, 2009, the contents of which are incorporated herein by reference.

TECHNICAL FIELD AND BACKGROUND OF THE INVENTION

The present invention relates to a multi-way valve, more particularly 2, 3 and 4-way valves, as used especially in medicine, and a method of producing such a multi-way valve.

Multi-way valves, more particularly 2, 3 and 4-way valves are known in the prior art and are used especially in medicine and medical technology. They are used especially for infusions, for artificial feeding and, in particular, for the supply and/or transfer of various throughflow media and as injection equipment for medical and pharmaceutical machines. The multi-way valves are also used in medical systems which comprise several components. Such systems include gravity infusions, pumps and pump transfer systems, tube feeding systems, injections, combinations thereof and suchlike.

Through being combined with several multi-way valves, a multi-way valve can be assembled into a multi-way valve bank or manifold (multiple distributor).

When providing multi-way valves it is particularly important that they exhibit a predetermined impermeability, are simple to use and that the components are burr-free. It must be especially taken into consideration that multi-way valves are used for the supply of various media which may be of very different viscosities.

Among the drawbacks of the multi-way valves known in the prior art is the fact that in various types of application they exhibit weaknesses, including in terms of their impermeability, user friendliness and problems with the throughflow of media of differing viscosities.

In addition, the multi-way valves for the flow of fluids known in the prior art also have the disadvantage that they are, among other things, made of plastics, during the processing of which softening agents such as bisphenol-A are used. When using the fluid throughflow valves it cannot be ruled out that particles of the softening agent are given off into the fluid, whereby it is known that these softening agents can lead to harm to human health. Among other things such softening agents are ascribed effects on the hormone balance and/or carcinogenic effects.

A further disadvantage of the fluid connections known in the state of the art is that in use they are in part applied more or less openly, so that, more particularly when no fluid is being administered to the patient, they come into contact with the air in the treatment room or even with other objects and persons, and are thereby contaminated with germs. In certain circumstances this contamination can result in severe infections of the persons to be treated.

The aim of this invention is to at least partially overcome the drawbacks known in the prior art.

SUMMARY OF THE INVENTION

The above objective may be achieved by way of a multi-way valve in accordance with one or more embodiments of the invention. The objective may also be achieved by a method of producing a multi-way valve of this type as well as using a multi-way valve in medicine and/or medical technology. In addition the objective may be achieved through the use of appropriate materials for the production of at least the surface which come into contact with the fluid. Preferred forms of the multi-way valve, as well of the method of producing the multi-way valve form the subject matter of other embodiments.

The multi-way valve in accordance with the invention for use in medicine and/or medical technology has a basic housing, through which a medium can flow at least in sections, and an actuator held in the basic housing so as to be rotatable about a central axis. The multi-way valve in accordance with the invention is characterised in that it has connection points for the inflow and outflow of the medium.

The basic housing of the multi-way valve in accordance with the invention also forms an actuator receptacle which is characterised in that it has a peg arranged concentrically in relation to the central axis of the basic housing, was well as a cut-out running radially around the inner side of the basic housing. The actuator of the multi-way valve in accordance with the invention has an operating element, as well as an essentially hollow cylindrical section, which holds the peg of the actuator receptacle of the basic housing at least in sections, at least one throughflow opening for the fluidic connection of at least two connection points and on the outer side of the hollow cylindrical section at least one radially encircling moulding.

The peg of the basic housing of the multi-way valve in accordance with the invention is designed in such a way that in the area of one connection of the basic housing it has or provides a counterbearing for the actuator which together with the actuator forms a sealing surface in the area of at least one connection point. The multi-way valve in accordance with the invention is characterised in that the peg of the basic housing has at least one flattened section on the circumference in relation to the central axis and the moulding of the actuator engages in the cut-out of the actuator receptacle of the basis housing in order to fix the actuator in the actuator receptacle in a positively locking and fluid-tight manner.

Medium in the sense of the present invention is taken to mean all types of fluids, more particularly fluids such as aqueous liquids, blood, liquid food etc. as well as gases.

The term basic housing in the sense of the present invention is taken to mean a component of the multi-way valve which has the housing with the connection points and the actuator receptacle, whereby the latter is taken to mean the area of the basic housing which holds the actuator.

Actuator in terms of the present invention is taken to mean a valve plug closing off at least one flow opening. The operating element in terms of the present invention is an element firmly connected to the actuator, for example a tap with which the actuator can be turned about the central axis. This can have one or more, usually two, three or four, setting levers.

A flattened section in the circumference of the peg is taken to mean a change in the annular circumference of the peg in the form of a chord of circle in a view from above, whereby the flattened sections forms a corresponding surface.

In a further form of embodiment of the multi-way valve in accordance with the invention the basic housing has two, three or four connection points.

In accordance with a further, particularly preferred form of embodiment the medium flowing through the multi-way valve is fluids, more particularly selected from a group including solutions for injection, solutions for infusion, nutrient solutions, blood, plasma as well as combinations thereof.

In accordance with another, particularly preferred form of embodiment the fluid flowing through the multi-way valve has a viscosity which is between 0.7 mPa·s and $10^6$ mPa·s, preferably between 1 mPa·s and $10^5$ mPa·s and particularly preferably around $10^2$ mPa·s.

In accordance with a further form of embodiment of the multi-way valve the peg of the basic housing is conical, at least in sections. In another, particularly preferred form of embodiment conical and non-conical and/or conical sections with different cone angles are arranged in a stepped sequence. The cone angle in accordance with the present situation is understood as a deviation for the central axis, more particularly cone angle is taken to mean positive and negative angles. In a further, particularly preferred form of embodiment the peg has an alternating sequence of positive and negative cone angles. In another preferred form of embodiment the peg has sections, more particularly conical section, inwardly and outwardly offset relative to the central axis.

In accordance with a further preferred form of embodiment, the inner side of the hollow cylindrical section is conical at least in sections, and more particularly, is essentially adapted to the conical shape of the peg.

In accordance with the present invention the throughflow openings of the actuator are designed in the form of a gate, more particularly in such a form that the throughflow opening is open towards the end of the hollow cylindrical section of the actuator. In addition, the size of the throughflow opening in particular is preferably adapted in relation to the fluid used, whereby a combination of the shapes of the counterbearing, for example conical and rectangular is also taken into consideration.

In accordance with another particularly preferred form of embodiment of the multi-way valve according to the invention, the number of throughflow openings in the actuator corresponds to the number of connection points on the basic housing. Thus, for example, a form of embodiment with two connection points has two throughflow openings. In accordance with a further preferred form of embodiment the actuator has fewer throughflow openings than there are connection points present on the basic housing, whereby at least, and more particularly, two throughflow openings or throughflow openings in the form of gates are provided.

In accordance with another preferred form of embodiment of the multi-way valve according to the invention, the hollow cylindrical section of the actuator has two, three or four mouldings radially encircling the central axis and the inner side of the actuator receptacle has a corresponding number of cut-outs.

In accordance with a further particularly preferred form of embodiment of the multi-way valve in accordance with the present invention the centre of the flattened section of the peg is offset in the actuator receptacle of the basic housing by 30° to 60°, more particularly by 45° to the connection point of the basis housing, whereby the lateral edge of the flattened section are arranged offset by ±20° ±1°, preferably ±15° ±2° and over around ±10° from the centre of the flattened section.

In accordance with another particularly preferred form of embodiment of the multi-way valve according to the invention, the counterbearing for the actuator is for by a non-flattened section of the peg. The modification of counterbearing receptacle by the one of more flattened sections on the peg in accordance with the invention results in a reduction in the friction surface between the peg and the actuator. This ensures ease of movement (user-friendliness) of the multi-way valve and at the same time guarantees that the valve cannot be displaced from a defined, set position by the used, more particularly, viscous medium.

Counterbearing in the sense of the present invention is taken to mean an area of the actuator which takes up the pressure on the actuator, particularly in the closed state and/or counters deformation of the actuator under the pressure of the medium.

In accordance with a further, particularly preferred form of embodiment of the multi-way valve in accordance with the present invention, the radially encircling mouldings on the hollow cylindrical section of the actuator and the cut-out on the inner side of the actuator receptacle form a retaining joint, whereby, in particular, the retaining joint has a retaining ring on the casing. In accordance with another preferred form of embodiment the retaining ring has a radially circumferential sealing section and/or positioning section. More particularly, the retaining joint between the actuator and the basic housing is such that by connecting the two sections a seal of greater than 4 bars is achieved.

In accordance with a further preferred form of embodiment of the multi-way valve in accordance with the invention at least the housing and/or the actuator is at least partially produced from a material selected from a group which in addition to copolyester includes other materials such as duroplastic and thermoplastic synthetic materials, more particularly polylphenyl sulphide, polypropylene, poly-1-butene, polyvinylchloride, polyvinylidene chloride, polymethyl metaacrylate, polyacryl nitre, polystyrene, polysulphone, polyacetal, polyvinyl alcohol, polyvinyl acetate, ionomers, fluoroplastics, polyethylene, polyamide, more particularly a partial aromatic polyamide, polycarbonate, polyester, copolyester, polyphenyl oxide, polysulphone, polyvinyl acetate, polyurethane and chlorinated polyether, cellulose nitrate, cellulose acetate, cellulose ether, phenol resin, urea resin, thiourea resin, melamine resin, alkyl resin, allyl resin, silicone, polyimide, polybenzimidazole, epoxy resin, casein plastic, cross-linked polyurethane, polyvinyl chloride, unsaturated polyester resin, antimicrobial or antiseptic material, for example highly porous silver, ion-free silver, silver compounds and in particular micro-silver, metal ion-releasing compounds and materials which do not contain softening agents, more particularly no bisphenol A or phthalates, as well as combinations thereof and suchlike.

In accordance with another preferred form of embodiment the multi-way valve according to the invention is characterised in that at least the surfaces of the connection system coming into contact with fluid, more particularly the inner surfaces of the multi-way valve are at least in parts made of a material which has antiseptic and/or antimicrobial properties.

Such antimicrobial or antiseptic materials are, for example, materials such as highly porous silver, ion-free silver, silver compounds and in particularly micro silver, metal-ion releasing compounds, combinations thereof and suchlike. Preferably these are arranged in the area of the relevant surfaces, whereby in accordance with a further particularly preferred form of embodiment the relevant materials are also incorporated into the synthetic material of which the multi-way valve and/or its components is/are made. Thus, more particularly, a highly porous silver which is preferably also ion-free, can be mixed into the synthetic material of which the components of the multi-way valve are then produced, at least in parts. Alternatively, in the context of the present invention the surfaces can also be coated with an appropriate material or combination of materials.

In accordance with another particularly preferred form of embodiment of the present invention an amorphic copolyester is used to produce a multi-way valve for use in medicine and medical technology in particular for infusion and transfusion tubes, multi-way valves, multiple distributors, injection equipment such as needles, accesses or suchlike and combinations thereof. The system is characterised in that at least the surface of the connection system combining into contact with fluid are at least in section made of an amorphic copolyester.

In accordance with another particularly preferred form of embodiment at least in parts materials are used for the production of the connection system according to the invention which do not contain any softening agents, more particularly no phthalates and no bisphenol A.

The objective of the present invention is also achieved through a method of producing a multi-way valve which comprises at least the following steps. In a preferably first step of the method according to the invention the basic housing as well as the actuator is produced, whereby the project preferably takes place using the injection moulding method. After taking up the basis housing in an assembly device in accordance with the invention method, the hollow cylindrical section of the actuator is introduced and pressed into the actuator receptacle of the basic housing. In the method in accordance with the invention the pressing in process is ended on reaching a predetermined press-in depth. More particularly, the press-in depth is determined by a defined stop. The impermeability of the valve in accordance with the invention is determined by the defined press-in depth. Thus the impermeability in the upper section is achieved through the defined press-in depth in the joint edge. In the inside of the housing the impermeability in relation to the corresponding throughflow openings is assured via the press-in depth and thus by the conical counterbearing.

In accordance with another particularly preferred form of embodiment the stop determining the press-in depth is an integral part of the circumferential moulding of the hollow cylindrical section of the actuator and/or part of the actuator receptacle of the basic housing; more particularly the stop is an integral part of the retaining joint.

In accordance with a further particularly preferred form of embodiment the peg forming the counterbearing is hollow at least in parts or, in accordance with a another particularly preferred form of embodiment is made of solid material.

In accordance with a further particularly preferred form of embodiment the deformations occurring during the joining of the components using the method according to the invention are essentially elastic deformations.

The present invention also consists in the use of the multi-way valve in accordance with the invention in medicine and in medical technology, more particularly for the supply and transfer or various throughflow media, more particularly for gravity infusion, for pump transfer systems, tube feeding systems, injections as well as combinations thereof and suchlike.

The invention will be explained below by way of a preferred example of embodiment, whereby it is pointed out that this example also covers derivations or additions directly evident to a person skilled in the art. Furthermore, this preferred example of embodiment does not represent a restriction of the invention, in that derivations and additions are within the scope of the present intention.

It is to be understood that the aspects and objects of the present invention described above may be combinable and that other advantages and aspects of the present invention will become apparent upon reading the following description of the drawings and detailed description of the invention.

DETAILED DESCRIPTION OF THE PRESENT INVENTION

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

Figure 1:
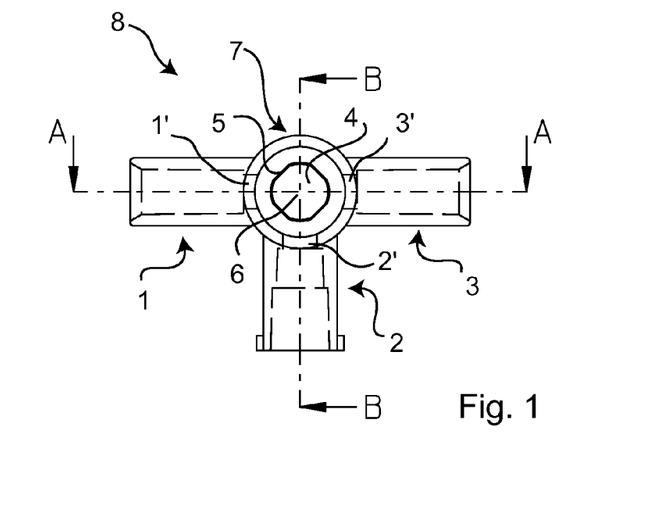
FIG. 1 shows a top view of a basic housing of a multi-way valve in accordance with the invention.

The example of embodiment in accordance with FIG. 1 shows the basic housing 8 with three connection points 1, 2, 3 and throughflow openings 1', 2', 3' corresponding thereto in the actuator receptacle 7. In the actuator receptacle 7 a peg 4 with four flattened section 5 is arranged around a central axis 6. The broken lines mark cross-section lines A-A and B-B for the cross-sections in FIGS. 2 and 3.

Figure 2:
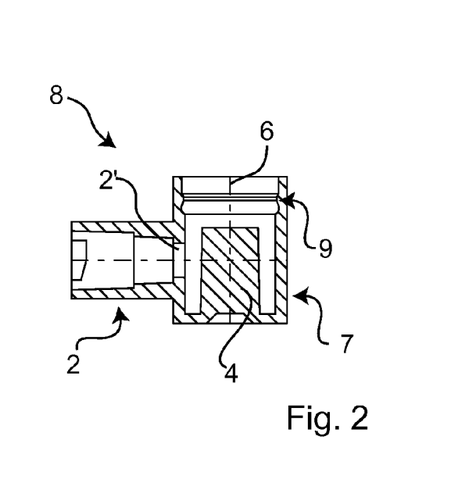
FIG. 2 shows a cross-section through the basic housing in FIG. 1 in the direction of line B-B.

Thus FIG. 2 shows a cross-section of the basic housing in the direction of the line B-B. The peg 4 is arranged around the central axis 7 in the actuator receptacle 6. The connection point 2 is connected to the actuator receptacle, forming the throughflow opening 2'. The inner side of the actuator receptacle 6 has a radially encircling cut-out 9, whereby the cut-out 9 is designed so that it has different depths.

Figure 3:
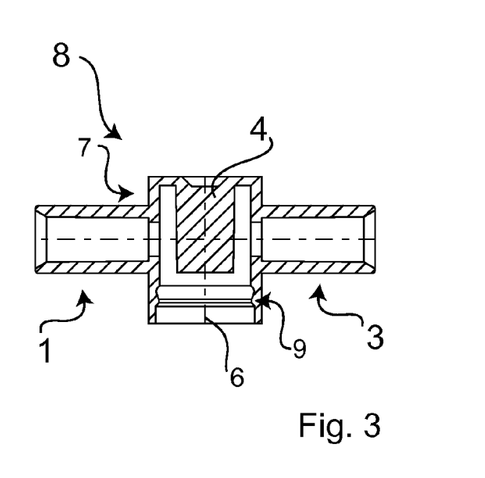
FIG. 3 shows a cross-section through the basic housing in FIG. 1 in the direction of line A-A.

FIG. 3 shows a cross-section of the basic housing in accordance with FIG. 2 in the direction line A-A marked in FIG. 1. The two connection points 1 and 3 are connected to the actuator receptacle, whereby the throughflow openings 1' and 3' are formed. The inner side of the actuator receptacle 6 has a radially encircling cut-out 9, whereby the cut-out 9 is designed so that it has different depths.

Figure 4:
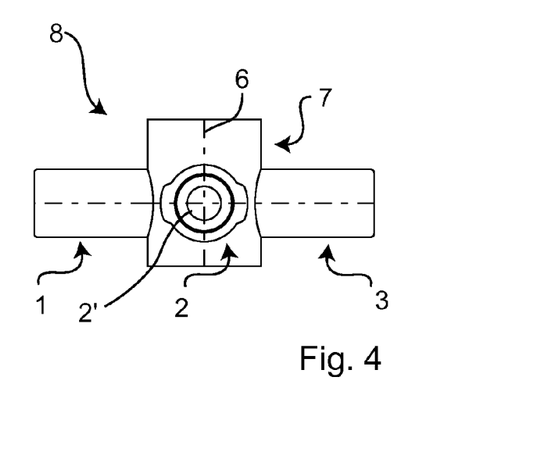
FIG. 4 shows a front view of the basic housing in FIG. 1.

FIG. 4 shows a side view from the front of the basic casing in accordance with FIG. 1. The connection points 1, 2, 3 are connected to the actuator receptacle 6. In the middle of these connections are the corresponding throughflow openings, such as throughflow opening 2' in connection point 2.

Figure 5:
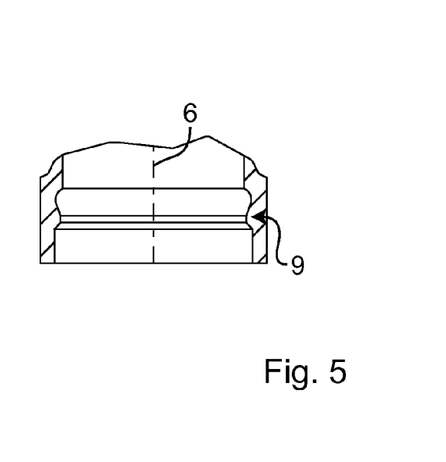
FIG. 5 shows a detailed view of the radially encircling cut-out of the actuator receptacle of the basic housing.

FIG. 5 show a part of the actuator receptacle 6 with the circumferential cut-out 9 on its inner side. The cut-out has various depths so that a sequence of recesses and bulges is formed.

Figure 6:
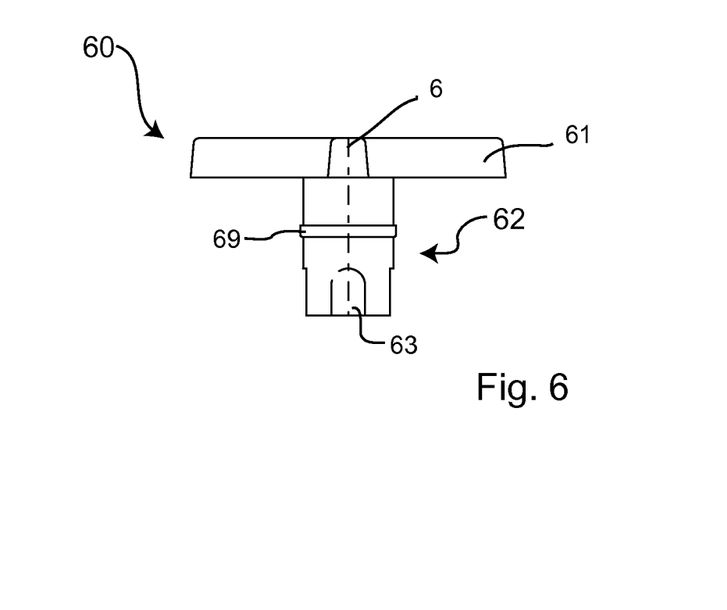
FIG. 6 shows an actuator of a multi-way valve in accordance with the invention.

FIG. 6 shows a form of embodiment of an actuator for use in connection with the basic housing in accordance with FIG. 1. The actuator has an operating element 61 in the form of a tap with three setting levers, which is firmly connected to a hollow cylindrical section 62. The hollow cylindrical section is arranged concentrically around a central axis 62. Formed on the end of the hollow cylindrical section opposite the operating element are gate-like throughflow openings 63. The number of throughflow openings 63 of the actuator corresponds to the number of connection points on the basic housing. Arranged on the hollow cylindrical section 62 of the actuator 60 is a radially encircling moulding 69.

Figure 7:
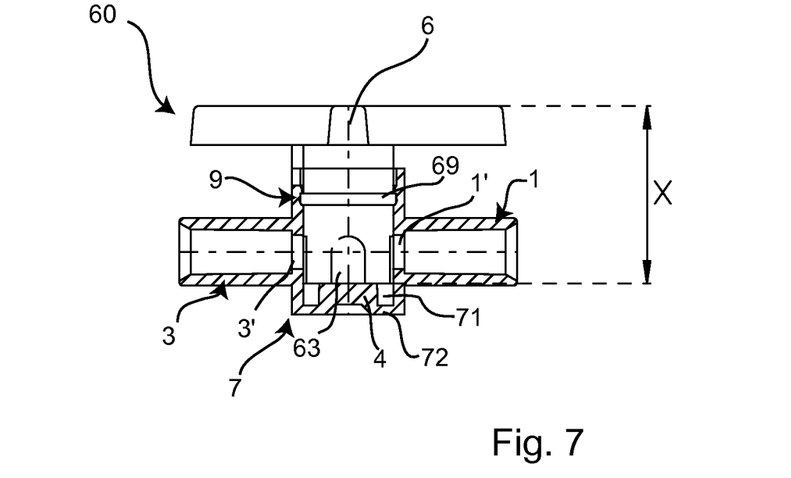
FIG. 7 shows a partial cross-section through the basic housing in FIG. 1 in the direction of line A-A with the pressed-in actuator.

FIG. 7 shows a connection of the basic housing (shown hatched) in accordance with FIG. 1 with the actuator 60 in accordance with FIG. 6 as a form of embodiment of the multi-way valve in accordance with the invention. The actuator 60 is pressed into the actuator receptacle 7 of the basic casing up to a predetermined press-in depth X. In this position the moulding 69 of the hollow cylindrical section of the actuator 60 engages in the cut-out 9 on the inner side of the actuator receptacle 6 of the basic casing. The hollow cylindrical section of the actuator 60 comprises the peg 4 of the actuator receptacle 6 arranged around the central axis 6 and thus forms a counterbearing for the actuator 60. The throughflow of the medium in the open position of the multi-way valve takes place from one of the connection points 1, 3 through the corresponding throughflow opening of the basic casing 1', 3' through a gate-like throughflow opening of the actuator 63 via a free space 71 between the actuator 60 and the base 72 of the actuator receptacle 6 to another throughflow opening 62 of the actuator and through the corresponding other throughflow opening 1', 3' of the basic casing from the other connection point 1, 3 on the basic casing. Impermeability in the upper section is achieved through a defined press-in depth of the actuator 60 into the joint edge. In the inside of the basic housing 8 the impermeability to the corresponding throughflow openings 1, 2, 3 is assured via the conical counterbearing formed by the peg 4. The ease of movement of the tap, i.e. the easy movement of the actuator 60 in the actuator receptacle 7 is ensured by the four flattened sections 5 on the peg 4.

Figures 8, 9:
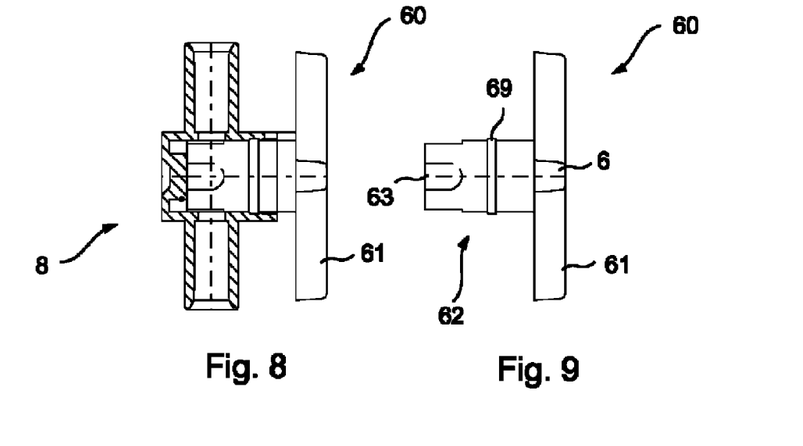
FIGS. 8 to 12 show a side view and top view of differently designed multi-way valves.
Figure 10:
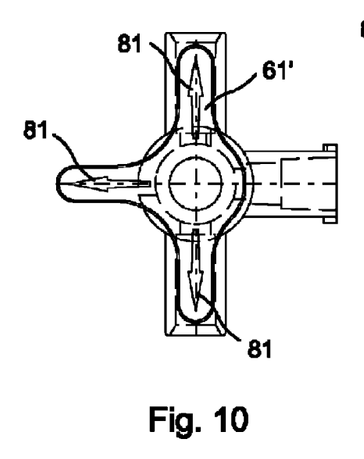
Figure 11:
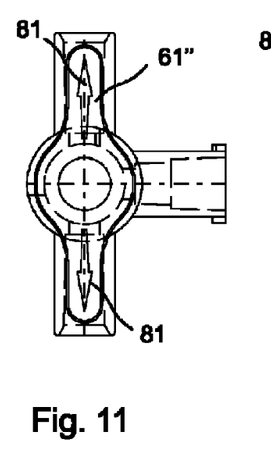
Figure 12:
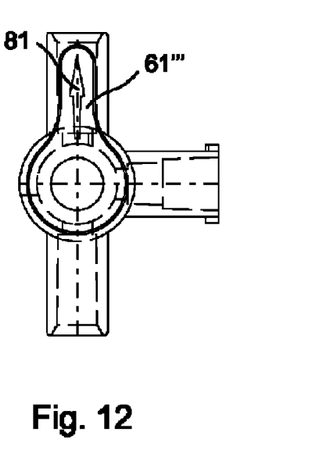

FIGS. 8 to 12 show a side view in each of FIGS. 8 and 9 and a top view in each of FIGS. 10 to 12 of differently designed multi-way valve, in which, in particular the operating elements 61', 61", 61''' are designed differently. Thus, FIG. 10 shows an operating element 61' with three arms, FIG. 11 shows operating element 61" with two arm and FIG. 12 shows an operating element 61''' with one arm, as can be used more particularly in combination with differently designed basic housings 8. The arrows 81 on the operating element are for easier orientation when using multi-way valve in practice by schematically indicating the flow direction of the fluid.

Figure 13:
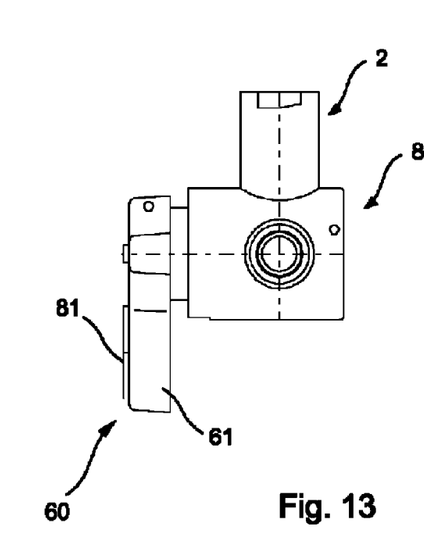
FIGS. 13 to 15 show a side view and top view of a particularly preferred form of embodiment of the multi-way valve.
Figure 14:
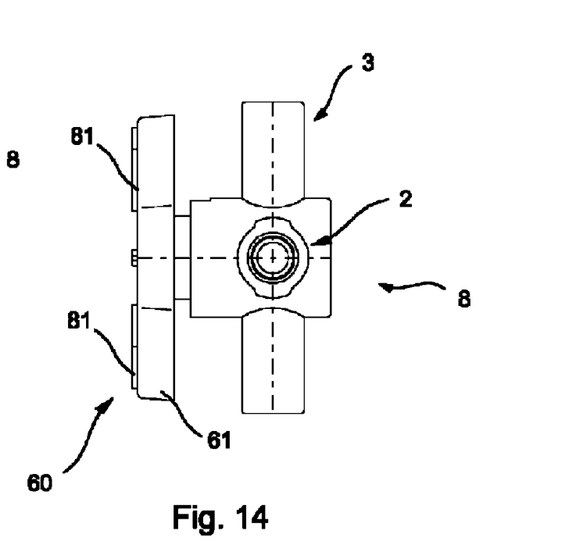
Figure 15:
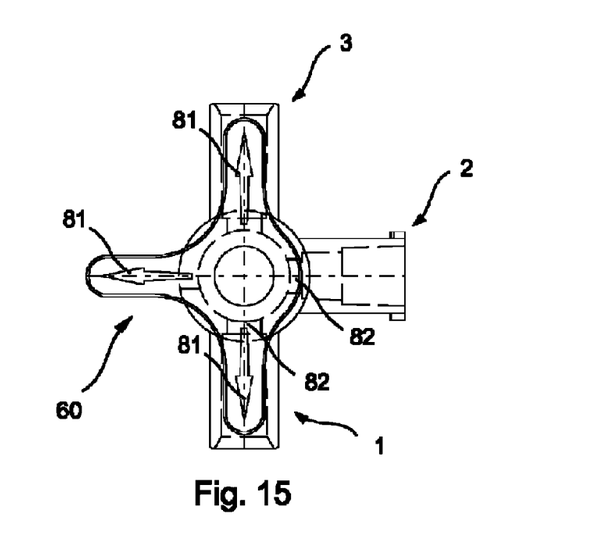

FIGS. 13 to 15 show a further form of embodiment in two side views (FIGS. 13 and 14) and a top view (FIG. 15). The essential elements are again shown in accordance with the above illustrations. In addition, the form of embodiment shown here shows an actuator 60 in which in the hollow cylindrical section 62 (not shown) only two openings 82 (gates) are provided, which are, more particularly, arranged at an angle of 90° to one another. In accordance with this embodiment, connections 1 and 2 or 2 and 3 are fluidically connected, depending on the setting. A connection between connection 3 and 1 is not possible.

Figure 16:
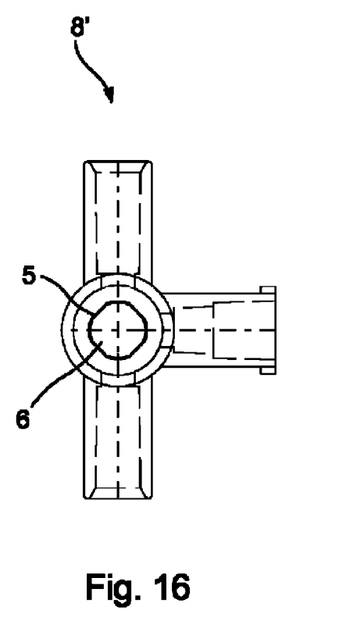
FIGS. 16 to 18 show top view of differently designed basic housing of the multi-way valve in accordance with the invention.
Figure 17:
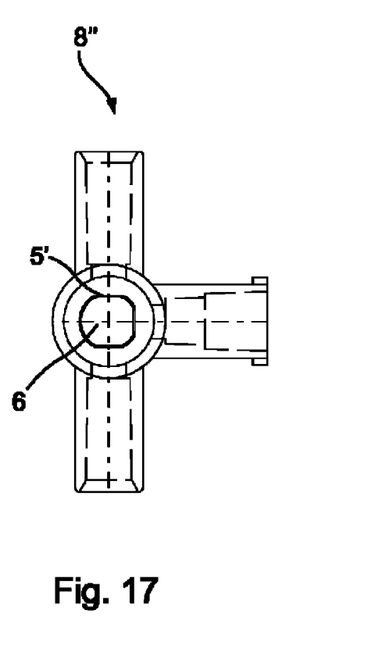
Figure 18:
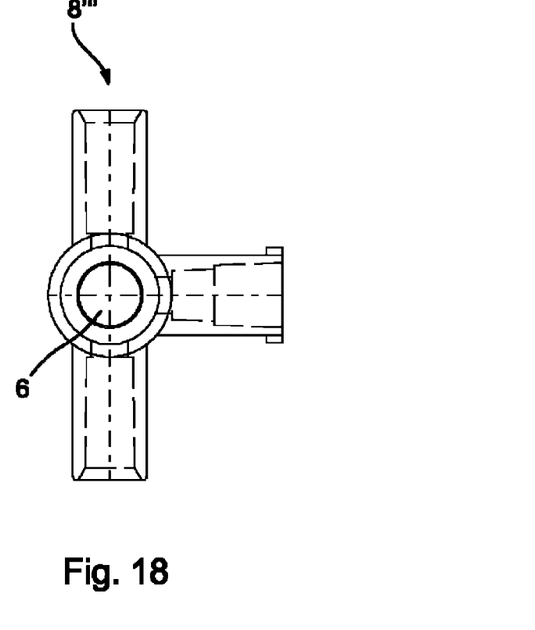

FIGS. 16 and 17 show top view of differently designed basic casings of the multi-way valve in accordance with the invention, whereby the central axis 6 differs in its design. Thus, FIG. 16 shows a central axis with four flattened sections 5, FIG. 17 a central axis 6 with three flattened sections 5 and FIG. 18 a central axis 6 without flattened sections. It should be taken into account that particularly the form of embodiment in accordance with FIG. 16 is suitable for parenteral applications the form of embodiment in accordance with FIG. 17 is more particularly suitable for use with large tube and/or greater volumetric throughputs.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A multi-way valve for use in medicine or medical technology with at least one basic housing through which a medium can flow at least in sections and in which an actuator is held in a rotating manner about a central axis, whereby
   the basic housing has at least two connection points for the inflow and outflow of the medium and forms an actuator receptacle which has a peg arranged concentrically in relation to the central axis and on the inside of the basic housing a radially encircling cut-out, and
   the actuator has an operating element and an essentially hollow cylindrical section which holds the peg of the actuator receptacle at least in sections, has at least one throughflow opening for the fluidic connection of at least two connection points and, on the outer side of the cylindrical section, at least one radially encircling moulding and
   the peg of the actuator receptacle has at least one counterbearing for the actuator to form a sealing surface in the area of at least one connection point, wherein
   the peg has at least one flattened area on the circumference in relation to the central axis, and the peg extends, from the base, over the height of the throughflow openings, and the moulding of the actuator engages in the cut-out of the actuator receptacle in order to fix the actuator in the actuator receptacle in a positive-locking and fluid-tight manner and the throughflow openings of the actuator are designed as gates which are open at the end of the hollow symmetrical section of the actuator.

2. The multi-way valve in accordance with claim 1, wherein the basic housing has two, three or four connection points.

3. The multi-way valve in accordance with claim 1 wherein the medium is a fluid which is selected from a group which includes solutions for injection, solutions for infusion, feeding solutions, blood, plasma, gases, and combinations thereof.

4. The multi-way valve in accordance with claim 3, wherein the fluid has a viscosity which is between 0.7 mPa·s and 106 mPa·s.

5. The multi-way valve in accordance with claim 1 wherein the peg, at least in sections, is designed conically.

6. The multi-way valve in accordance with claim 1 wherein the inner side of the cylindrical section of the actuator, at least in sections is designed conically and more particularly essentially corresponds with the conical course of the peg.

7. The multi-way valve in accordance with claim 1 wherein the number of throughflow openings of the actuator corresponds with the number of connection points in the basic housing.

8. The multi-way valve in accordance with claim 1 wherein two, three or four mouldings, radially encircling the central axis, are provided in the hollow cylindrical section of the actuator and a corresponding number of cut-outs in the actuator receptacle.

9. The multi-way valve in accordance with claim 1 wherein the middle of the flattened area on the peg is arranged offset in relation to the connection point by 30° to 60°, and the edges of the flattened area are offset from the middle of the flattened area by ±20° ±1°.

10. The multi-way valve in accordance with claim 1 wherein the counterbearing for the actuator is formed by a non-flattened area of the peg.

11. The multi-way valve in accordance with claim 1 wherein the circumferential moulding in the hollow cylindrical section of the actuator and the cut-out in the actuator receptacle form a retaining joint which has a retaining ring on the housing.

12. The multi-way valve in accordance with claim 11, wherein the retaining ring has a radially circumferential sealing section and/or positioning section.

13. The multi-way valve in accordance with claim 1 wherein at least the basic housing and/or the actuatorare at least partially made of a material which is selected from a group which in addition to copolyester includes duroplastic and thermoplastic synthetic materials, polylphenyl sulphide, polypropylene, poly-1-butene, polyvinylchloride, polyvinylidene chloride, polymethyl metaacrylate, polyacryl nitre, polystyrene, polysulphone, polyacetal, polyvinyl alcohol, polyvinyl acetate, ionomers, fluoroplastics, polyethylene, polyamide, more particularly a partial aromatic polyamide, polycarbonate, polyester, copolyester, polyphenyl oxide, polysulphone, polyvinyl acetate, polyurethane and chlorinated polyether, cellulose nitrate, cellulose acetate, cellulose ether, phenol resin, urea resin, thiourea resin, melamine resin, alkyl resin, allyl resin, silicone, polyimide, polybenzimidazole, epoxy resin, casein plastic, cross-linked polyurethane, polyvinyl chloride, unsaturated polyester resin, antimicrobial or antiseptic material, for example highly porous silver, ion-free silver, silver compounds, metal ion-releasing compounds and materials which do not contain softening agents, as well as combinations thereof.

14. A method of producing a multi-way valve comprising the steps:
   producing the basic housing and the actuator;
   placing the basic housing and the actuator in an assembly device;
   inserting and pressing in of the hollow cylindrical section of the actuator into the actuator receptacle on to a peg that extends, from the base, over the height of the throughflow openings; and,
   ending the pressing-in procedure on reaching a predetermined pressing-in depth, which is determined in particular by a defined stop.

15. The method in accordance with claim 14, wherein the stop is an integral part of the circumferential moulding in the hollow cylindrical section of the actuator and/or the cut-out in the actuator receptacle and more particularly the retaining joint.

16. The method in accordance with claim 15 wherein the deformations when joining the components are essentially elastic deformations.

17. Use of the multi-way valve in accordance with claim 13 in medicine and/or medical technology for the supply and/or transfer of various fluid media, pump transfer systems, feeding tube systems, injections, and combinations thereof.

* * * * *